United States Patent
Wesselmann et al.

(10) Patent No.: US 9,770,575 B2
(45) Date of Patent: Sep. 26, 2017

(54) BALLOON CATHETER, IN PARTICULAR FOR DELIVERING DRUGS OR STENTS IN THE REGION OF A STENOSIS

(75) Inventors: Matthias Wesselmann, Glattfelden (CH); Tobias Brunner, Zurich (CH); Hans Lang, Buchs (CH)

(73) Assignee: Biotronik AG, Buelach (CH)

( * ) Notice: Subject to any disclaimer, the term of this patent is extended or adjusted under 35 U.S.C. 154(b) by 97 days.

(21) Appl. No.: 13/283,050

(22) Filed: Oct. 27, 2011

(65) Prior Publication Data

US 2012/0116490 A1 May 10, 2012

Related U.S. Application Data

(60) Provisional application No. 61/411,485, filed on Nov. 9, 2010.

(51) Int. Cl.
*A61M 25/10* (2013.01)
*A61F 2/958* (2013.01)
*A61F 2/966* (2013.01)

(52) U.S. Cl.
CPC ......... *A61M 25/1006* (2013.01); *A61F 2/958* (2013.01); *A61F 2/966* (2013.01); *A61M 2025/105* (2013.01); *A61M 2025/1061* (2013.01); *A61M 2025/1068* (2013.01); *A61M 2025/1081* (2013.01); *A61M 2025/1093* (2013.01)

(58) Field of Classification Search
CPC ... A61F 2/958; A61F 2/966; A61M 2025/105; A61M 2025/1061; A61M 2025/1068; A61M 2025/1081; A61M 2025/1093; A61M 25/1006

USPC ........ 604/97.01, 103.02, 104–109, 913–921; 606/191–200
See application file for complete search history.

(56) References Cited

U.S. PATENT DOCUMENTS

| | | | | |
|---|---|---|---|---|
| 4,922,905 A | * | 5/1990 | Strecker | .................... A61F 2/24 606/195 |
| 5,102,402 A | * | 4/1992 | Dror | ....................... A61F 2/958 604/103.02 |

(Continued)

FOREIGN PATENT DOCUMENTS

| | | |
|---|---|---|
| EP | 0 292 587 A1 | 5/1987 |
| EP | 1 836 998 A1 | 3/2007 |

*Primary Examiner* — Nathan R Price
*Assistant Examiner* — Weng Lee
(74) *Attorney, Agent, or Firm* — Wagenknecht IP Law Group PC

(57) ABSTRACT

A balloon catheter, in particular for delivering medicaments, stents or medicament-coated stents in the region of a stenosis, comprising
an outer shaft (4)
an inner shaft (6), and
a balloon (7) at the distal catheter end, which balloon is dilatable by a feedable pressure fluid and which is attached with its proximal end (8) to the outer shaft (4) and with its distal end (9) to the inner shaft (6) which protrudes the outer shaft (4) in the distal direction, and
a cover sheath (15) which is seated in a covering position over the contracted balloon (7) and is displaceably guided on the outer shaft (4) and which is displaceable on the outer shaft (4) in the proximal direction via its front opening (17) by the dilating balloon (7) while continuously releasing the same from distal to proximal.

11 Claims, 8 Drawing Sheets

(56) References Cited

U.S. PATENT DOCUMENTS

| | | | | |
|---|---|---|---|---|
| 5,817,057 A | * | 10/1998 | Berenstein | A61M 25/007 |
| | | | | 604/95.01 |
| 5,830,181 A | * | 11/1998 | Thornton | A61M 25/104 |
| | | | | 604/102.01 |
| 6,544,223 B1 | * | 4/2003 | Kokish | 604/103.01 |
| 6,702,843 B1 | * | 3/2004 | Brown et al. | 623/1.11 |
| 2002/0045914 A1 | * | 4/2002 | Roberts | A61F 2/958 |
| | | | | 606/192 |
| 2005/0080474 A1 | | 4/2005 | Andreas et al. | |

* cited by examiner

BALLOON CATHETER, IN PARTICULAR FOR DELIVERING DRUGS OR STENTS IN THE REGION OF A STENOSIS

CROSS REFERENCE TO RELATED APPLICATIONS

This invention claims benefit of priority to U.S. patent application Ser. No. 61/411,485, filed on Nov. 9, 2010; the contents of which are herein incorporated by reference in their entirety.

TECHNICAL FIELD

The invention relates to a balloon catheter, in particular for delivering medicaments or stents in the region of a stenosis, the balloon catheter having an outer shaft, an inner shaft and a balloon at the distal catheter end, which balloon is dilatable by a feedable pressure fluid. The balloon is attached with its proximal end to the outer shaft and with its distal end to the inner shaft which protrudes the outer shaft in the distal direction.

BACKGROUND

With respect to the background of the invention it is to be noted that for delivering stents in the region of stenoses or lesions in a body vessel or for releasing medicaments in such body regions, catheters of different designs are used. US 2009/0018501 shows a balloon catheter, the balloon of which is coated with a medicament. The balloon is arranged in the manner of a rolling membrane between outer and inner shaft. When inserting the catheter into the body, the inner shaft is displaced relative to the outer shaft in the proximal direction so that the balloon is covered between outer and inner shaft. At the site of use, the balloon is then inflated by means of a pressure fluid, wherein the outer shaft is displaced relative to the inner shaft in the proximal direction and the balloon opens like a rolling membrane in a rolling and shearing manner and dilates. The problem here is the fact that during opening the rolling membrane balloon, the membrane of the same is subjected to very small bending radii and high shear forces so that the coating with the active ingredient can be peeled off the balloon in an uncontrolled manner. Moreover, when the balloon opens, or already on the way to the site of use, losses of active ingredients can occur.

In connection with the delivery of stents, US 2009/0259286 A1 shows a catheter with a stent which, during the insertion of the catheter, is retained in the contracted position underneath a sheath at the distal end. Said sheath is configured such that when the balloon dilates and thereby the stent expands, it breaks along a predetermined path. This requires a relatively complicated and error-prone design of the sheath. Accordingly, the positioning of the stent can be inaccurate.

Finally, from US 2005/0033402 A1, a delivery device for a stent is known wherein the latter is arranged and covered underneath a sheath during the insertion. For releasing the stent, the sheath is provided with a pull wire by means of which the sheath can be pulled away on the proximal side and accordingly, a release of the stent can be achieved. This, of course, requires an extremely complicated construction of the catheter. Further, the pull wire is susceptible to breaking. In this case, releasing the stent is not possible anymore.

In EP 0 596 145 B1, a method is described by means of which the retention force of the stent on the catheter is achieved by means of embossing the stent pattern under the influence of temperature. Because the balloon shortens under the thermal effect, the embedding with this method is only optimal in the case if the stent itself is embedded in the balloon under thermal effect and the stent is virtually "frozen" in the balloon material. For stents coated with medicaments, this method can only be applied as long as the glass temperature of the balloon material lies far below the degradation temperature of the medicament.

From U.S. Pat. No. 7,651,525 B2, a stent device is known in which a catheter has an outer sheath which extends from the distal to the proximal end and in the distal end region of which, a self-expanding stent is arranged on a dilatable balloon in the contracted state. To deliver the stent, the outer sheath is pulled back manually by a practitioner or by a mechanical actuation in the proximal direction relative to the stent. The latter is positioned in a body vessel while inflating the balloon and self-extracting at the treatment site.

SUMMARY

Based on the described problems of the prior art, the object underlying the invention is to improve a balloon catheter for delivering medicaments or stents in such a manner that this can be carried out reliably and accurately and with simple handling and low constructional efforts for the catheter, and that it is gentle to the active ingredient in the case of a medicament release.

This object is solved by the balloon catheter, wherein a cover sheath is provided which is seated in a covering position over the contracted balloon and is displaceably guided on the outer shaft and which is displaceable on the outer shaft in the proximal direction via its front opening by the dilating balloon while continuously releasing the same from distal to proximal.

Due to this configuration, no separate mechanism is necessary for releasing the balloon by pulling the cover sheath back; in fact, the cover sheath is automatically displaced by the dilating balloon, whereby the balloon is continuously released. Since this releasing process starts from the distal end of the balloon, the balloon catheter can anchor itself in the vessel on the other side of a stenosis so that thereby the blood flow in the vessel is stopped. Thus, in particular a self-expanding stent can be accurately positioned and can be delivered without the tendency to spring during opening.

With this catheter, medicament-coated stents can be reliably transported underneath the cover sheath to the stenosis without the need that the stent has to be embedded separately in the balloon. The thermal load of the medicament coating which is necessary for fixing the stent on the balloon thus is eliminated. If stent segments tend to stand up ("fish scaling") when passing through narrow curves, the cover sheath ensures that said segments do not get caught in the body or at the guide catheter thereby stripping off the stent.

Also, no separate actuation of the cover sheath is necessary because the same is displaced virtually automatically by the balloon. In the case of a balloon having a medicament coating, due to the balloon dilating from the distal end and the resulting anchoring of the balloon in the vessel thereby stopping the blood stream, no loss of active ingredients is involved because no blood stream is present which could wash off the medicament. When releasing the balloon—in contrast to the aforementioned rolling membrane balloon—the coating is not subjected to narrow bending radii and shearing connections.

According to preferred embodiments of the invention, the axial friction force between balloon or, respectively, stent and sheath can be significantly reduced by generating a counter pressure to the inner pressure of the balloon in the region between balloon and sheath. For this purpose, the cover sheath is preferably displaceably guided in a pressure-tight manner on the outer shaft.

Finally, the pressure equalization in the intermediate space between cover sheath and balloon can be carried out with the pressure fluid used to dilate the balloon, for example in such a manner that the intermediate space between cover sheath and balloon communicates with the pressure fluid line to the balloon via a passage opening in the outer shaft.

According to a further preferred embodiment of the invention, the balloon catheter can be used to place self-expanding stents. For this purpose, the stent is retained in the contracted state on the balloon by the cover sheath in the covering position and is gradually released through the dilating of the balloon.

According to an alternative embodiment, the cover sheath serves for a securely covered transport of the active ingredient-coated balloon to the region of the stenosis and—as already mentioned above—for a gentle release of the active ingredient.

According to a further preferred embodiment, a limit stop is arranged on the outer shaft for limiting the displacement path of the cover sheath in the proximal direction. Thus, the movability of the cover sheath can be limited in such a manner that it is clamped between the cone of the dilated balloon and the limit stop so that a good sealing between the front opening of the cover sheath and the balloon cone is achieved. Then, the balloon can be pressurized with the maximum target pressure without the risk that the pressure fluid escapes through the intermediate space, which is pressurized as well, between balloon and cover sheath.

Stripping off the cover sheath in the distal direction can be constructionally prevented by a dead stop which is larger than the proximal cover sheath diameter. The dead stop can be generated as a ring which is crimped on or glued on, or by deforming the outer shaft.

To facilitate a reliable gradual opening of the balloon during dilatation from distal to proximal it is of advantage that in the covering position of the cover sheath, an initial opening gap for the balloon remains between the front opening and a cone body at the distal end of the inner shaft.

The secure emptying of the balloon during deflation can be ensured by two measures: on the one hand, by setting a higher flow resistance in the direction towards the cover sheath, e.g., by an outlet opening which is only very small compared to the large flow cross-section in the direction towards the balloon or, on the other, by supplementing a check valve with a very thin, resilient ring-shaped membrane which is shrunk on the outside of the outer shaft over the outlet hole. When inflating, said membrane lifts off and supplies the cover sheath with the necessary counter pressure. When deflating with a maximum of 1 bar pressure difference, the membrane securely closes the outlet hole. Both measures can also be combined.

DESCRIPTION OF THE DRAWINGS

Further features, details and advantages of the invention arise from the following description of an exemplary embodiment based on the enclosed drawings. In the figures.

DETAILED DESCRIPTION

Figure 1:
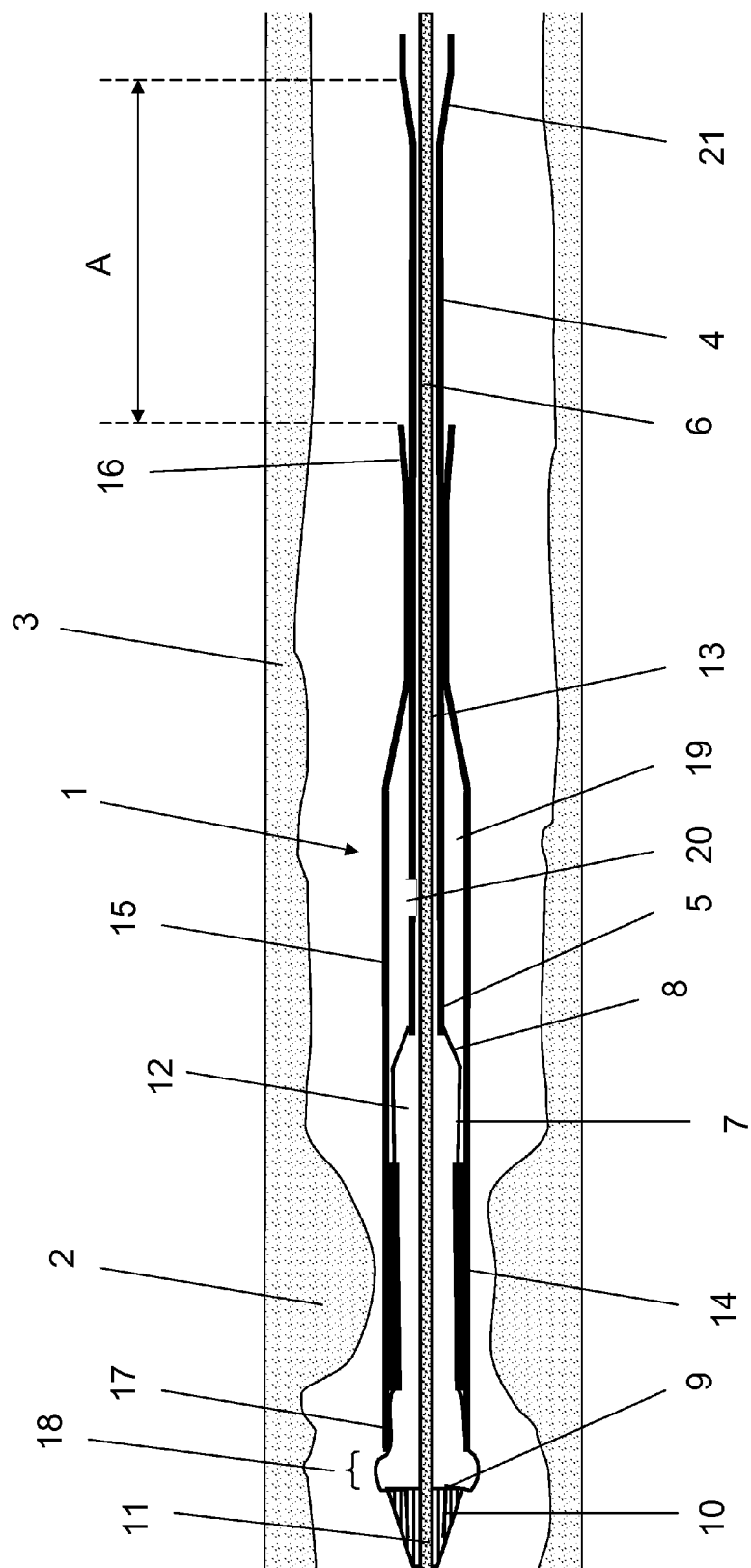
FIGS. 1 to 8 show schematic longitudinal axial sections of the distal end of a balloon catheter in the region of a vascular stenosis in successive dilatation steps of the balloon.

Collectively, FIGS. 1-8 show the distal end region of a balloon catheter 1 which is placed in the region of a stenosis 2 in a body vessel 3. The balloon catheter 1 has an elongated, flexible outer shaft 4 and an inner shaft 6 running therein and extending beyond the distal end 5 of the inner shaft 4, which inner shaft is also made of a flexible material. A balloon 7 which can be dilated by a pressure fluid is fastened at the distal catheter end in a pressure tight manner with its proximal cone 8 to the distal end 5 of the outer shaft 4 and with its distal cone 9 to the cone body 10 at the distal end 11 of the inner shaft 6.

Via the annular space 13, the balloon volume 12 can be pressurized between outer and inner shaft 4, 6 with a pressure fluid.

In the drawings, the hatched area designated with the reference number 14 indicates a coating with a medicinal active ingredient or stent which is to be applied by means of the dilatable balloon 7 in the region of the stenosis.

Finally, the balloon catheter 1 is provided at its distal end with a cover sheath 15 which is displaceably guided in the direction of the longitudinal axis on the outer shaft 4. The cover sheath 15 is seated over the balloon 7 which is contracted and folded in the position according to FIG. 1 and protects the latter together with the coating/stent 14 when inserting the catheter into the body vessel 3. As is apparent from FIG. 1, the balloon 7 emerges via the front opening 17 at the distal end of the cover sheath 15, wherein between the front opening 17 and the cone body 10 an initial opening gap 18 remains through which the balloon cone can emerge to the outside.

The cover sheath 15 protrudes the balloon 7 in the proximal direction and thus forms an intermediate space 19 behind the balloon 7 where a passage opening 20 in the outer shaft 4 communicates with the pressure fluid line formed by the annular space 13. Thus, with the pressurization of the balloon 7, the intermediate space 19 is pressurized at the same time so that between balloon 7 and the cover sheath 15, a counter pressure is generated which counteracts a "wedging" effect between the balloon 7 and the cover sheath 15.

With distance A to the proximal end 16 of the cover sheath 15, an annular circumferential dead stop 21 is provided on the outer shaft 4. The distance A defines the maximally possible displacement path of the cover sheath 15 on the catheter in the proximal direction.

The operating mode of the balloon catheter 1 is now to be described as follows:

In the configuration shown in FIG. 1, the balloon catheter is advanced to the shown stenosis 2 in the body vessel 3. Here, the coating/stent 14 is properly stored within the cover sheath 15, and the balloon 7 is kept at its minimum diameter. Due to said storage, the catheter has a profile with a small area even after passing narrow radii. In particular, no so-called "fish scaling" of a stent 14 seated on the balloon 7 occurs in narrow curves. Furthermore, a separate embedding of a stent 14 on the stent 7 is no longer necessary due the cover sheath 15.

Figure 2:
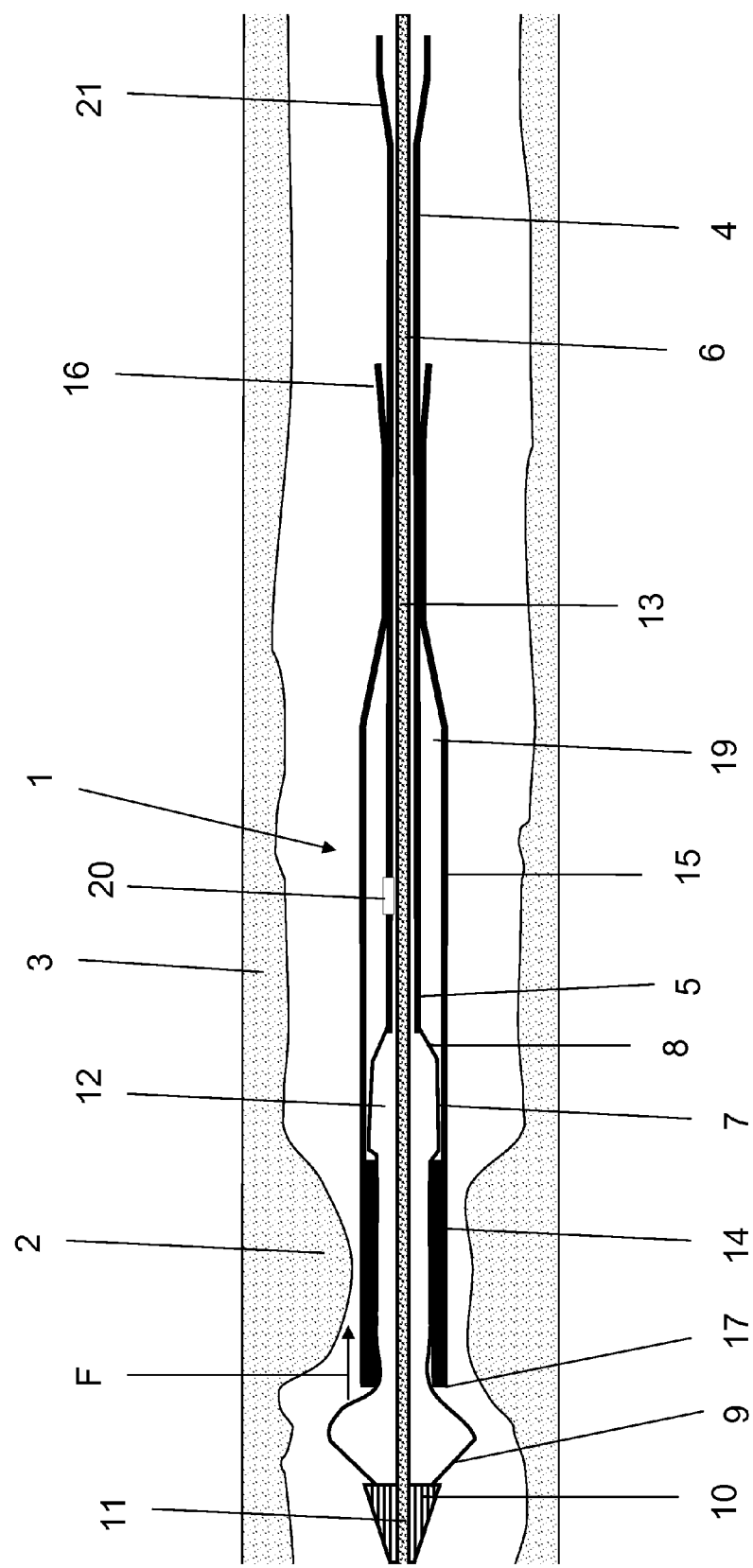
Figure 3:
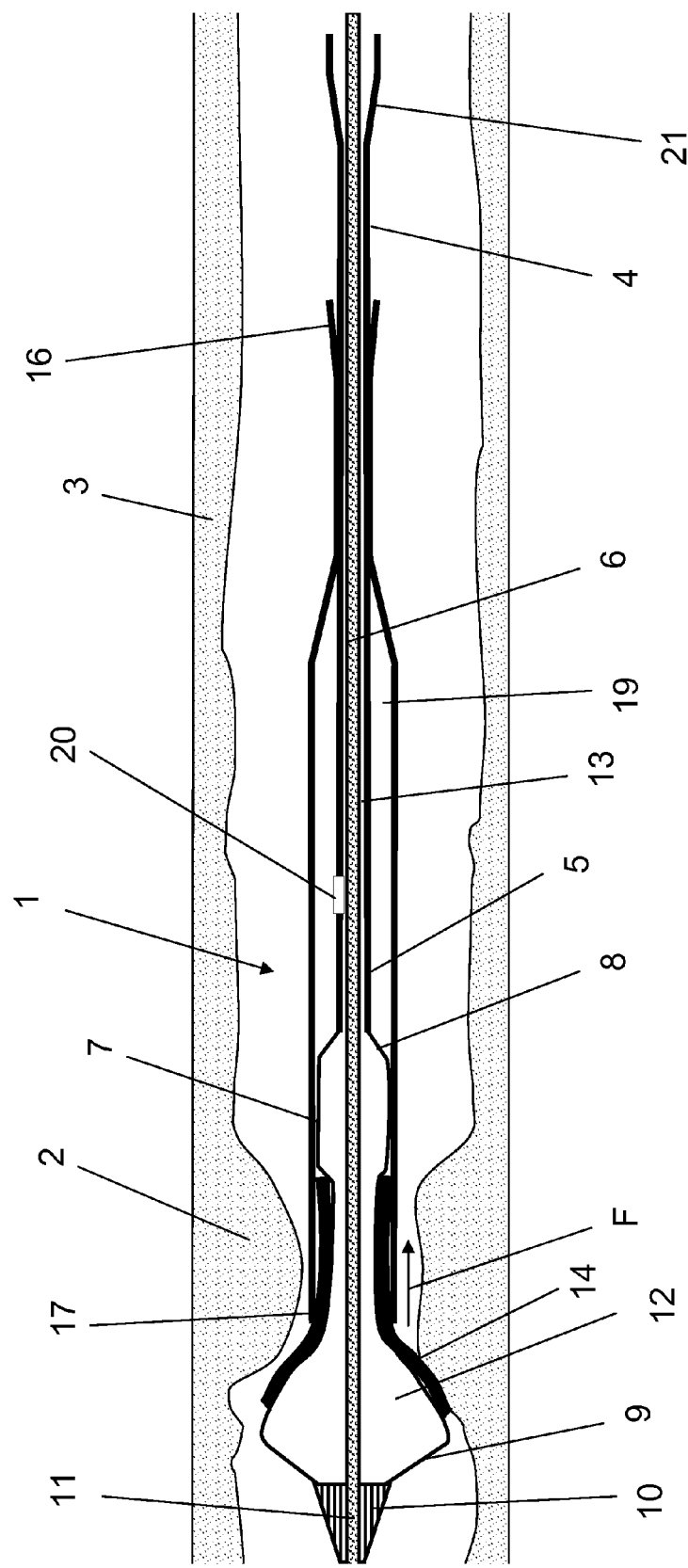
Figure 4:
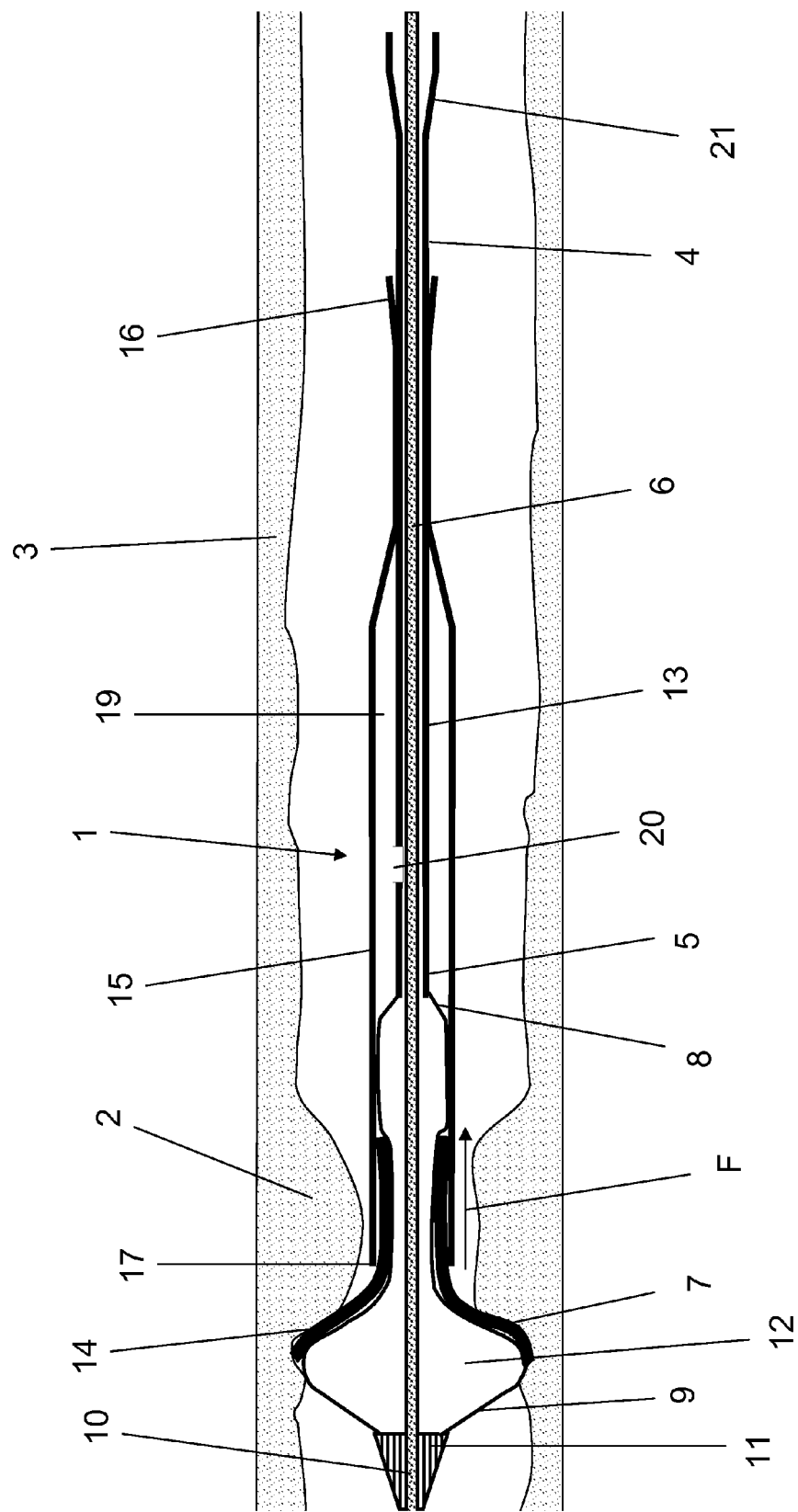

Upon reaching the target position in the region of the stenosis 2, as shown in FIG. 2, the balloon 7 is pressurized by introducing a pressure fluid via the annular space 13. The balloon 7 begins to expand in the initial opening gap 18, whereby at the same time, a stripping force F on the cover sheath 15 is generated in the axial direction towards proximal. The cover sheath 15 thus slides back on the outer shaft 4 and continues to release the balloon 7 while the same continues to dilate. (see FIGS. 2 and 3).

Since the balloon 7 expands at the distal end of the catheter in front of the stenosis 2, the balloon with the coating/stent 14 is distally anchored in front of the stenosis 2 (FIG. 4) so that then the blood flow through the body vessel 3 is stopped. Active ingredients in the coating 14 are thus not washed out and therefore a smaller dosage can be achieved there.

Figure 5:
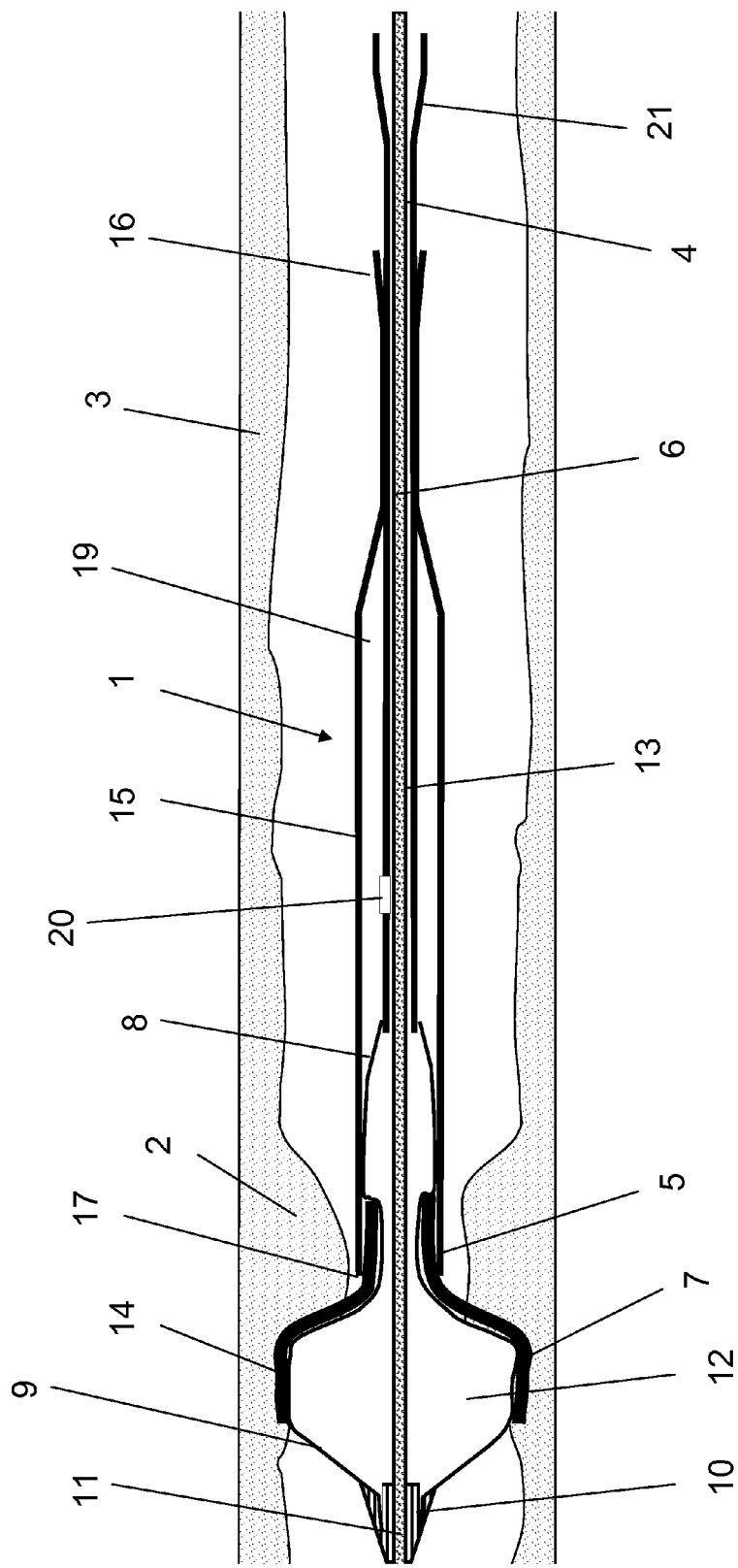
Figure 6:
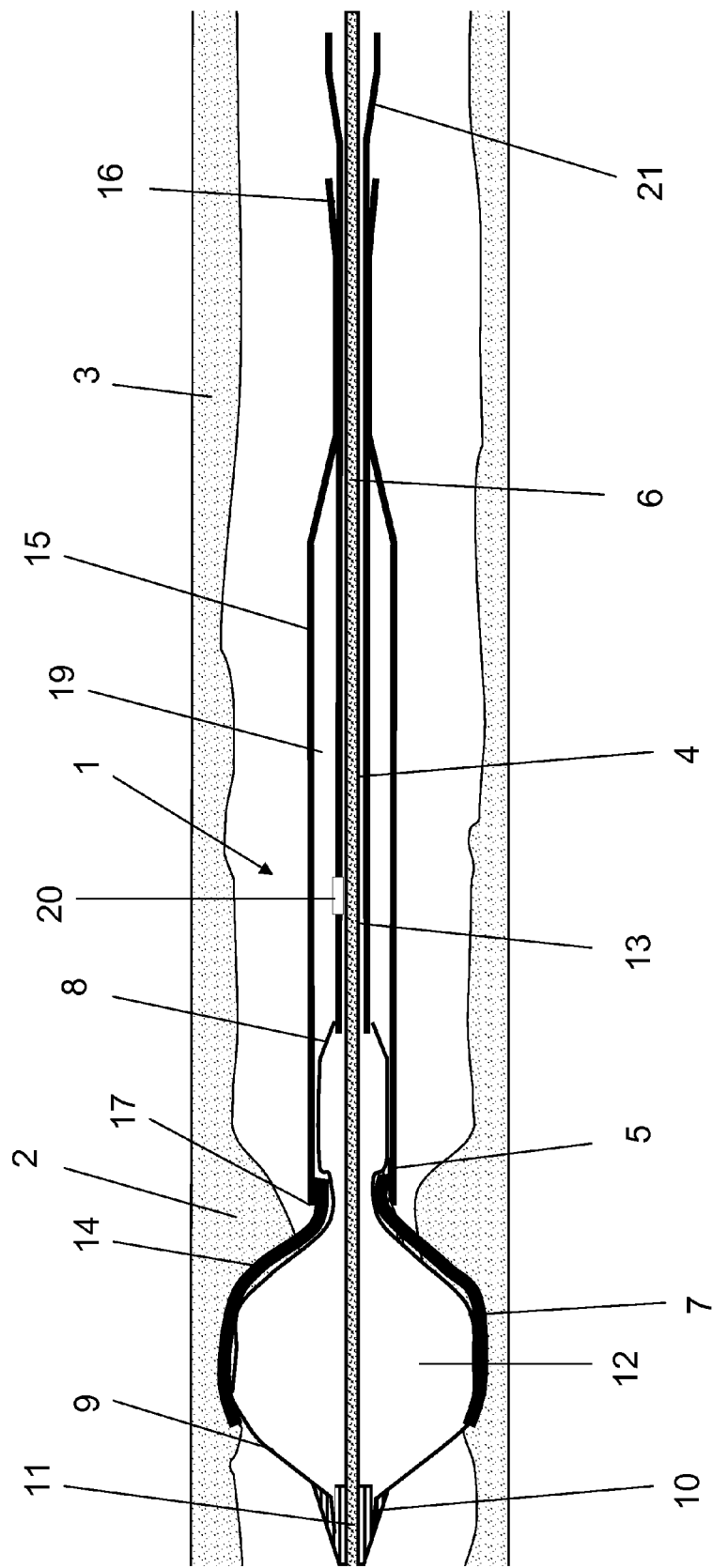
Figure 7:
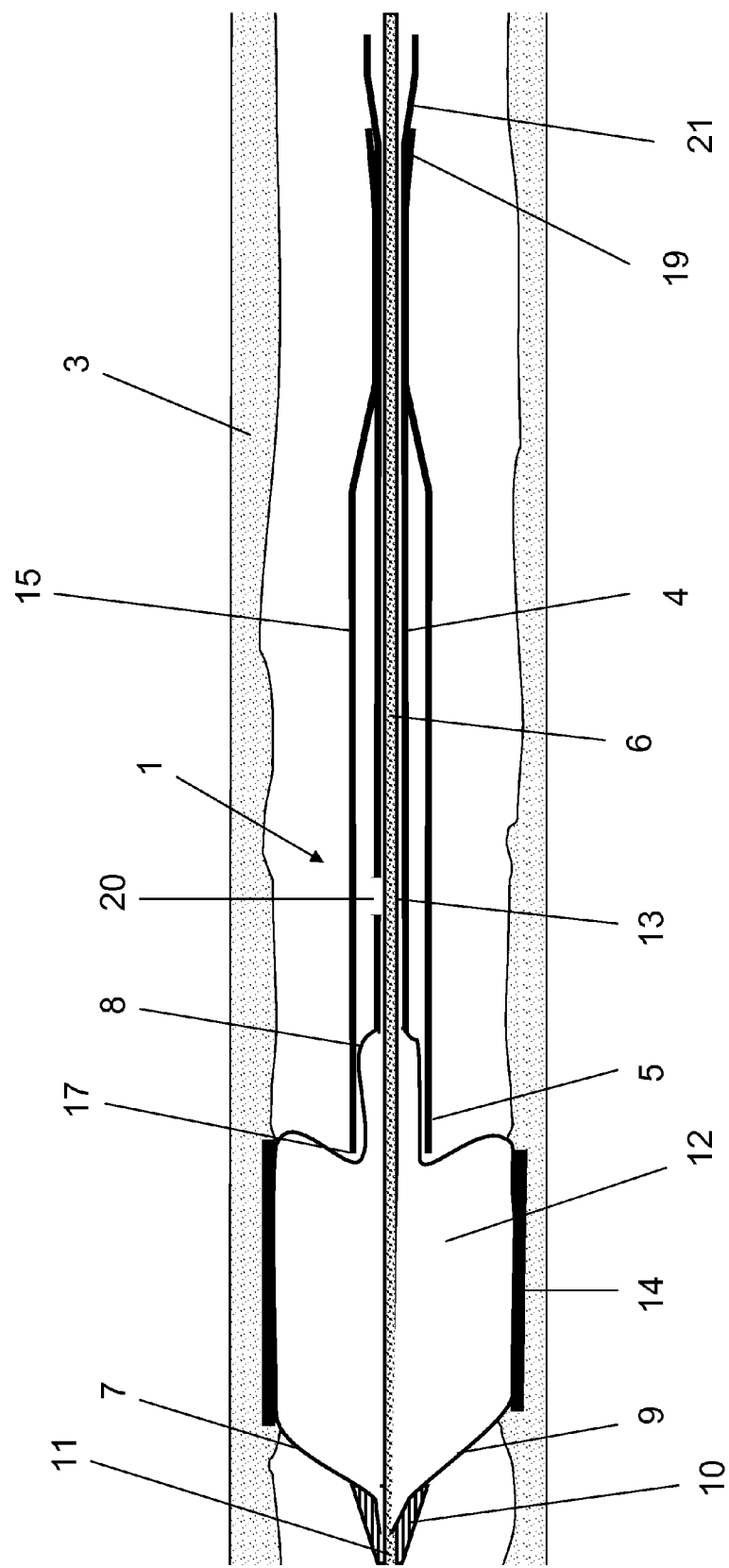
Figure 8:
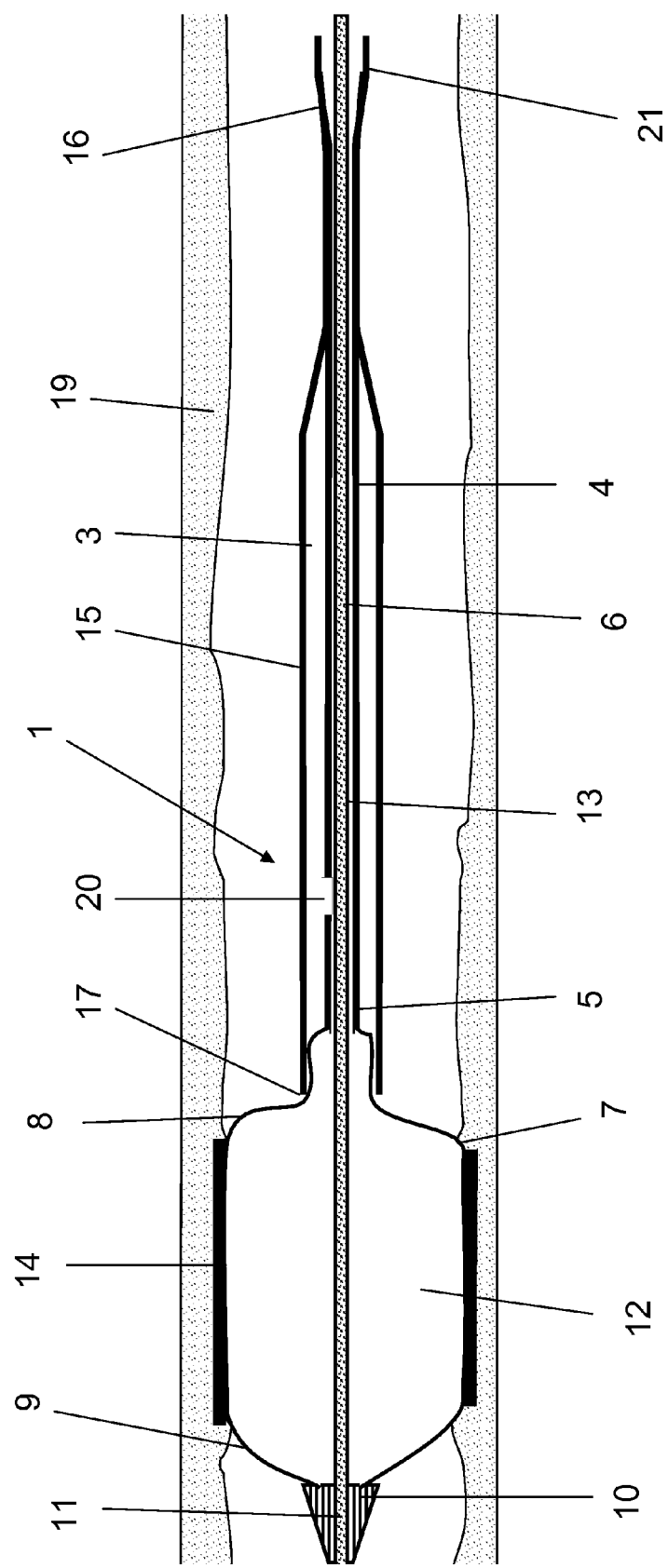

With increasing expansion of the balloon 7, the sheath 15 is continuously displaced in the proximal direction and the coating/stent 14 is delivered in the region of the stenosis 2 and the latter is increasingly widened (FIGS. 5 and 6).

In the final phase of the dilatation of the balloon 7, the coating/stent 14 is finally applied on the body vessel 3 by means of the fully expanded balloon 7, whereby, at the same time, the stenosis 2 is removed (FIG. 7); the cover sheath 15 has finally reached its end position (FIG. 8) at the dead stop 21, whereby the proximal cone 8 of the balloon 7 can be supported at the front opening 7. The pressurized intermediate space 19 is thus sealed so that the balloon 7 can be pressurized with its full target pressure and can be completely dilated.

By pressure relief, the balloon 7 can contract again and the catheter 1 can be removed from the body.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A balloon catheter comprising:
   an outer shaft comprising a passage opening transverse to its length,
   an inner shaft,
   a balloon dilatable by a feedable pressure fluid through the outer shaft, wherein the proximal end of the balloon is attached to the outer shaft entirely distal to the passage opening to provide access to an intermediate space outside of the outer shaft without entering the balloon, further wherein the inner shaft protrudes from the outer shaft in a distal direction, and
   a cover sheath which is seated in a covering position over the passage opening and the balloon when the balloon is contracted, wherein during dilation of the balloon the cover sheath seals against both the outer shaft and the balloon in a pressure-tight manner and the balloon emerges from a front opening at a distal end of the cover sheath to displaceably guide the cover sheath along the outer shaft in a proximal direction via its front opening, thereby continuously releasing the dilating balloon from distal to proximal,
   wherein the intermediate space positioned between the cover sheath and the balloon communicates with a pressure fluid line to the balloon via the passage opening outside of the balloon.

2. The balloon catheter according to claim 1, characterized in that the intermediate space between the cover sheath and the balloon delivers pressurized fluid outside and proximal to the balloon to counteract wedging of the balloon against the sheath during dilation.

3. A balloon catheter loaded with a stent, comprising:
   an outer shaft comprising a passage opening transverse to its length,
   an inner shaft,
   a balloon dilatable by a feedable pressure fluid through the outer shaft, wherein the proximal end of the balloon is attached to the outer shaft entirely distal to the passage opening to provide access to an intermediate space outside of the outer shaft without entering the balloon, further wherein the inner shaft protrudes from the outer shaft in a distal direction,
   a cover sheath which is seated in a covering position over the passage opening and the balloon when the balloon is contracted, wherein during dilation of the balloon the balloon emerges from a front opening at a distal end of the cover sheath and displaceably guides the cover sheath along the outer shaft in a proximal direction via its front opening to continuously release the dilating balloon from distal to proximal, and
   a stent arranged on the balloon, which stent is retained in its contracted state enclosed by the cover sheath in the covering position of the latter and can be automatically released by the dilatation of the balloon while displacing the cover sheath at the same time in the proximal direction,
   wherein the intermediate space positioned between the cover sheath and the balloon communicates with a pressure fluid line to the balloon via the passage opening outside of the balloon.

4. The balloon catheter according to claim 1, characterized in that the balloon is provided on its outer side with a medicament coating which can be released in the proximal direction by the dilatation of the balloon while displacing the cover sheath at the same time.

5. The balloon catheter according to claim 1, characterized in that a dead stop is arranged on the outer shaft for limiting the displacement path of the cover sheath in the proximal direction while maintaining the seals.

6. The balloon catheter according to claim 1, characterized in that the balloon is attached with its distal end via a cone body to the inner shaft.

7. The balloon catheter according to claim 6, characterized in that in the covering position of the cover sheath, an initial opening gap remains for the balloon between the front opening of the cover sheath and the cone body.

8. The balloon catheter according to claim 3, characterized in that the balloon is provided on its outer side with a medicament coating which can be released in the proximal direction by the dilatation of the balloon while displacing the cover sheath at the same time.

9. The balloon catheter according to claim 3, characterized in that the balloon is attached with its distal end via a cone body to the inner shaft.

10. The balloon catheter according to claim 3, characterized in that a dead stop is arranged on the outer shaft for limiting the displacement path of the cover sheath in the proximal direction while maintaining the seals.

11. The balloon catheter according to claim 10, characterized in that in the covering position of the cover sheath, an initial opening gap remains for the balloon between the front opening of the cover sheath and the cone body.

* * * * *